(12) United States Patent
Van Brunt et al.

(10) Patent No.: US 9,695,806 B2
(45) Date of Patent: Jul. 4, 2017

(54) METHOD OF CONTROLLING GASEOUS FLUID PUMP

(75) Inventors: Nicholas P. Van Brunt, White Bear Lake, MN (US); John A. Kivisto, Oak Grove, MN (US); Theodore W. Jagger, White Bear Lake, MN (US)

(73) Assignee: Vbox, Incorporated, White Bear Lake, MN (US)

( * ) Notice: Subject to any disclaimer, the term of this patent is extended or adjusted under 35 U.S.C. 154(b) by 1510 days.

(21) Appl. No.: 12/839,997

(22) Filed: Jul. 20, 2010

(65) Prior Publication Data

US 2011/0020143 A1 Jan. 27, 2011

Related U.S. Application Data

(60) Provisional application No. 61/227,541, filed on Jul. 22, 2009.

(51) Int. Cl.
| | |
|---|---|
| *F04B 17/04* | (2006.01) |
| *F04B 19/22* | (2006.01) |
| *A61M 1/14* | (2006.01) |
| *F04B 27/00* | (2006.01) |
| *F04B 35/04* | (2006.01) |

(Continued)

(52) U.S. Cl.
CPC ............... *F04B 17/04* (2013.01); *A61M 1/14* (2013.01); *F04B 27/005* (2013.01); *F04B 35/045* (2013.01); *F04B 17/042* (2013.01); *F04B 2201/0201* (2013.01); *F04B 2203/0401* (2013.01); *F04B 2205/07* (2013.01); *F05C 2203/0808* (2013.01); *H02K 16/00* (2013.01); *H02K 33/16* (2013.01)

(58) Field of Classification Search
CPC ........ F04B 17/04; F04B 19/22; F04B 17/042; F05C 2203/0808; F15B 11/042; F15B 2211/20515; H02K 33/16
USPC ...................... 417/415–418, 419; 310/15–24
See application file for complete search history.

(56) References Cited

U.S. PATENT DOCUMENTS

| 3,327,633 A | 6/1967 | Duinker et al. | |
|---|---|---|---|
| 3,846,682 A * | 11/1974 | Massie | H02K 33/14 |
| | | | 310/31 |

(Continued)

FOREIGN PATENT DOCUMENTS

| JP | S60187253 A | 9/1985 |
|---|---|---|
| JP | 06185473 A | 5/1994 |

(Continued)

OTHER PUBLICATIONS

The Apr. 21, 2011 PCT International Search Report for International application No. PCT/US2010/042640.

(Continued)

*Primary Examiner* — Dominick L Plakkoottam
(74) *Attorney, Agent, or Firm* — Kinney & Lange, P.A.

(57) ABSTRACT

A method of controlling a fluid pump. The pump has a plurality of oscillating pistons that travel along a central axis of a piston sleeve. A plurality of pistons is of similar mass within a piston sleeve are provided, and adjacent pistons are positioned to be 180 degrees apart in phase oscillations. An electric coil is provided for each piston, and the position of adjacent pistons is determined. The current to one of the electric coils for a piston is adjusted to maintain the 180 degree difference in phase between oscillations of adjacent pistons.

14 Claims, 2 Drawing Sheets

(51) Int. Cl.
   *H02K 33/16* (2006.01)
   *H02K 16/00* (2006.01)

(56) References Cited

U.S. PATENT DOCUMENTS

| | | | | |
|---|---|---|---|---|
| 4,284,990 | A * | 8/1981 | Fowler | F02P 7/061 340/870.18 |
| 5,148,066 | A | 9/1992 | Beale et al. | |
| 5,201,573 | A * | 4/1993 | Leiber | B60T 8/26 303/113.4 |
| 5,203,172 | A * | 4/1993 | Simpson | F04B 17/042 180/305 |
| 5,228,840 | A | 7/1993 | Swank | |
| 5,342,176 | A | 8/1994 | Redlich | |
| 5,496,153 | A | 3/1996 | Redlich | |
| 5,537,820 | A | 7/1996 | Beale et al. | |
| 5,642,088 | A | 6/1997 | Unger | |
| 5,873,246 | A | 2/1999 | Beale | |
| 5,899,672 | A | 5/1999 | Salamey | |
| 6,199,381 | B1 | 3/2001 | Unger et al. | |
| 6,293,184 | B1 | 9/2001 | Unger | |
| 6,326,706 | B1 * | 12/2001 | Zhang | F04B 35/045 310/12.24 |
| 6,401,686 | B1 | 6/2002 | Prueitt et al. | |
| 6,536,326 | B2 | 3/2003 | Unger et al. | |
| 6,641,377 | B2 * | 11/2003 | Toyama | F04B 35/045 417/416 |
| RE38,337 | E | 12/2003 | Beale | |
| 6,920,967 | B2 | 7/2005 | Wood | |
| 7,318,506 | B1 * | 1/2008 | Meic | F02B 63/04 123/46 R |
| 7,453,241 | B2 | 11/2008 | Keiter et al. | |
| 7,768,160 | B1 * | 8/2010 | Sahyoun | H02K 33/16 310/14 |
| 7,823,381 | B2 * | 11/2010 | Misselhorn | F02G 1/0435 60/517 |
| 2001/0027087 | A1 | 10/2001 | Shiomi et al. | |
| 2001/0050079 | A1 * | 12/2001 | Piesinger | A62B 7/00 128/200.28 |
| 2004/0146417 | A1 | 7/2004 | Dunn | |
| 2005/0081804 | A1 * | 4/2005 | Graf | B60K 6/24 123/46 E |
| 2005/0082994 | A1 * | 4/2005 | Qiu | F16F 7/1011 318/128 |
| 2008/0012432 | A1 * | 1/2008 | Togare | H02K 7/075 310/24 |
| 2008/0080981 | A1 | 4/2008 | Witt et al. | |
| 2008/0164287 | A1 * | 7/2008 | Larsson | B67D 7/04 222/333 |
| 2008/0185045 | A1 * | 8/2008 | Erno | F03G 7/08 137/14 |
| 2008/0226477 | A1 | 9/2008 | Wu et al. | |
| 2009/0191073 | A1 * | 7/2009 | Kopecek | F04B 17/04 417/415 |
| 2010/0292631 | A1 * | 11/2010 | Holden | A61F 9/00745 604/22 |

FOREIGN PATENT DOCUMENTS

| | | |
|---|---|---|
| JP | 2006105058 A | 4/2006 |
| KR | 100742041 B1 | 8/2007 |

OTHER PUBLICATIONS

The Feb. 23, 2011 PCT International Search Report for the International Application No. PCT/US2010/042633.
Extended European Search Report for European Patent Application No. 10802794.7, dated Feb. 15, 2017, 7 pages.

* cited by examiner

METHOD OF CONTROLLING GASEOUS FLUID PUMP

CROSS-REFERENCE TO RELATED APPLICATIONS

Reference is made to the following pending applications: U.S. patent application Ser. No. 12/839,992 entitled "GASEOUS FLUID PUMP" as filed on even date herewith, and claims priority to U.S. Provisional Pat. App. Ser. No. 61/227,541 entitled "GASEOUS FLUID PUMP" filed Jul. 22, 2009, which is hereby incorporated by reference in its entirety.

BACKGROUND

This invention is an electronically powered gaseous fluid pump. It contains unique design features that combine to minimize its size, weight, power consumption and mechanical vibration.

This pump was developed for use in a portable oxygen concentrator that provides portable supplementary oxygen to patients with lowered blood oxygen levels. The concentrator is much lighter, smaller and quieter than competing devices and is the only one that can be conveniently worn by the user as they move about rather than wheeled on a cart or carried like a piece of luggage. The pump consumes most of the concentrator electrical power input, accounts for over half the total weight and is the largest component in the concentrator. Minimizing size, weight, power consumption and vibration of the pump contributed directly to the portability advantages of the concentrator. No commercially available pump would meet the size, weight and power consumption goals of that concentrator design. The pump design disclosed here can be scaled for larger or smaller pumping capacity and pressure ranges to provide benefits in other applications.

SUMMARY

Disclosed is a method of controlling a fluid pump. The pump has a plurality of oscillating pistons that travel along a central axis of a piston sleeve. A plurality of pistons of similar mass are provided within a piston sleeve, and adjacent pistons are positioned to be 180 degrees apart in phase oscillations. An electric coil is provided for each piston, and the position of adjacent pistons is determined. The current to the electric coils for the pistons is adjusted to maintain the 180 degree difference in phase between oscillations of adjacent pistons.

In another embodiment, an apparatus for pumping and compressing fluids has a cylinder body comprising a central axis, and an inner surface that creates an inner volume, a first piston and a second piston of similar mass within the cylinder, wherein the first and second pistons are able to oscillate along the central axis. The first and second pistons are driven by magnetic forces generated by electrical currents to oscillate the first and second pistons with a similar stroke length while maintaining a 180 degree difference between the oscillations of the first and second pistons.

In another embodiment, a method of controlling a fluid pump is disclosed. The pump has an oscillating piston that travels along a central axis of a piston sleeve. A length of the piston travel is controlled by multiplying an incremental step of a current pulse fed into a pump by a value that represents the desired stroke length and a value that represents the pressure difference between an inlet and an outlet of the pump.

DETAILED DESCRIPTION

Figure 1:
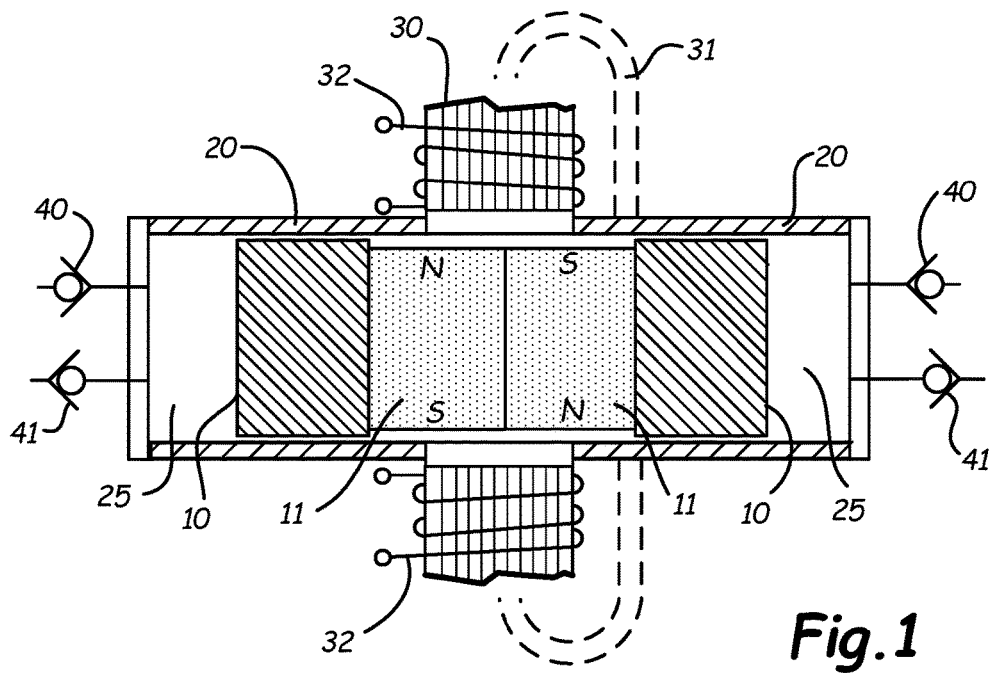
FIG. 1 is a cross sectional view of one embodiment of a pump.

The pump disclosed herein was developed for use in a portable oxygen concentrator that provides portable supplementary oxygen to patients with lowered blood oxygen levels. Initial efforts were directed toward identifying and minimizing the energy losses of a pump during the conversion of electrical energy to pneumatic energy. The specific application for the pump set forth design specifications that required a pump displacement rate of about 25 liters per minute and a 6:1 compression ratio. Other design criteria included continuous operation with no maintenance, and that the pump could not contaminate the gas flow with vapors, such as from lubricants. A 90% energy conversion efficiency goal was set. This is the pneumatic power of the pumped gas plus the adiabatic heating of the gas stream all divided by the total electrical input power. Pneumatic power is the gas flow rate times the pressure rise from the input to the output of the pump. For example, using Watts as the units of power, 1 Watt=(0.592 Liters/Minute flow)×(1 Atmosphere pressure rise). Adiabatic heating power would be the power in watts to heat the compressed output gas stream above the temperature of the low pressure input stream according to the pressure change, gas flow rate and specific heat of the pumped gas composition. Electrical input power in watts is 1 Watt=1 Amp×1 Volt.

The conversion efficiency losses of the pump would be distributed among fluid flow losses, gas leakage, mechanical friction between moving parts, mechanical vibration, electrical power losses through resistive motor coil windings, and losses in magnetic flux carrying steel components due to eddy currents and hysteresis.

Efforts were focused on positive displacement type pumps rather than blowers or turbines. Prior art indicated that blowers were not a good choice in the flow and pressure range that needed to operate within the design criteria. Dynamic gas flow losses and gas leakage are also known to be minor factors in the efficiency of displacement pumps. Efficient designs for flow paths, valve geometries, and sealing methods for displacement pumps are well known in the prior art. Study of prior art displacement pump designs along with experimental measurements revealed that friction in the structures that seal the moving displacement elements were a significant source of power loss. Common examples of the seal structures are piston rings, flexible diaphragms, sliding vanes, and scroll edge seals. Seal structures and materials were analyzed and tested, but significant improvement opportunities were not readily found.

Experiments were conducted with a piston and cylinder structure built from a unique combination of materials. A stationary glass cylinder containing a moving graphite piston was tested. The cylinder and piston surfaces were very smooth, round, and straight. The piston was formed to fit inside the cylinder with enough precision that leakage of gas past the clearance gap between the piston and cylinder walls was insignificant at the targeted flow and pressure. As the piston moved in the cylinder, a gaseous bearing formed in the clearance gap between the parts. This resulted in an extremely low dynamic coefficient of friction between the piston and cylinder.

The piston and cylinder were briefly in contact during start up until the gas bearing formed with significant relative motion between the piston and cylinder. The materials had to slide in contact without significant wear during this start up interval. The gap between the piston and cylinder had to be very small and stable as the pump operated to minimize leakage and to maintain the gas bearing. The piston and cylinder materials needed to have similar thermal expansion coefficients so the gap would remain nearly constant as temperatures changed. The materials needed to be rigid enough that the gap would not distort as gas pressures in the pump imparted variable forces on the piston and cylinder. Glass and graphite fit these limitations for the design criteria. Other materials with these characteristics can be substituted. Examples of other useful material choices could include metals or ceramics with low friction materials layered over the contact surfaces.

In one embodiment, the piston was to be driven with purely axial forces. Radial sidewall forces would cause the air bearing to collapse increasing friction and allowing wear if the piston and cylinder come into hard contact. A typical motor driven crank and connecting rod structure common to many pump designs converts the rotary motion of motors to the axial motion needed to drive a piston, but sidewall forces are exerted on the piston by these configurations. Additional guides and another joint can be added to the connecting rod, or a scotch yoke type of structure can be configured to eliminate sidewall forces between the piston and cylinder, but this would introduce additional friction producing elements offsetting the benefits of the simpler, very low friction, piston and cylinder with a gas bearing.

A head with valves was added to one end of the glass cylinder and connected the graphite piston to a linear motor. The motion of the motor was controlled by a programmable sequencer. The cylinder, piston, motor stroke, and cycle rate were sized to pump air at the pressure and flow range to meet design criteria.

The efficiency of this configuration was found to be very poor, and did not meet design criteria. Even when the pump was operated in free flow with no significant pressure rise at its output port the linear motor became quite hot indicating energy being lost in the motor. The energy loss was initially blamed on the linear motor design. The electrical resistance of the motor coils was too high for the amount of current the motor was drawing and the slide bearings in the motor seemed to introduce too much friction. After considering the problem and testing some ideas, design efforts were directed to drive the pump piston directly by magnetic forces acting through the wall of the glass cylinder. Strong neodymium permanent magnets were placed inside the piston close to but not touching the cylinder inner wall. A magnetic flux path made of steel laminations around the outer surface of the cylinder was positioned to provide a flux path between the north and south poles of the piston magnets. Multiple turns of electrical wire were wrapped around the steel flux path, and an electronic circuit driven by a microcontroller that could apply a programmable current waveform to the coil was designed.

FIG. 1 is a cross sectional diagram representing one embodiment of a pump. Graphite piston ends 10 are fit inside glass cylinder 20 with a small air gap as previously discussed. The piston ends 10 are bonded to cylindrical permanent magnets 11 with magnetic north and south poles arranged as indicated by N and S in the figure. Piston ends 10 and magnets 11 form a single rigid piston that moves in cylinder 20 sweeping through gas volumes 25. This displaces gas volumes 25 forcing any fluid contained therein out of the cylinder through valves 40 as the piston moves toward it, and into volume 25 through valves 41 as the piston moves away from it. Magnetic flux path 31 is formed by stacking multiple steal laminations 30. The shape of laminations 30 and path 31 is seen more clearly in the end view of FIG. 3. The flux path 31 can be a variety of shapes as long as it forms a path for magnetic flux lines between the north and south poles of the piston magnets 11. Electrical coils 32 are wound around core made of laminations 31. Coils 32 are connected so that current flows through them in series. Coils 32 are shown in the figures as two separate coils wound on laminations 31 positioned close to the cylinder. This proved to perform the best during testing, but different positions for coils 32 and a single coil also performed the desired function.

This configuration produces an axial force on the piston in direction and magnitude approximately proportional to the current applied to the coil. Each magnet pole is arranged so that it is either repelled or attracted by the magnetic flux in the gap between the steel flux path and the magnets when the flux is modified by the current in the electrical coil. The pump contains a near frictionless means of moving a piston in a cylinder driven by an electrical current to displace a gas volume. The only moving part in this combined motor and pump assembly is the piston, and the piston has a very low friction coefficient due to the air bearing between it and the cylinder.

With the cylinder material extending through the space between the permanent magnets and the steel core as shown in FIG. 1, the cylinder needs to be non magnetic to avoid disrupting the magnetic flux path between the steel core and the piston magnets. The cylinder also needs to have low electrical conductivity so that energy is not lost through eddy currents induced by rapidly changing magnetic flux in the space between the magnets and the core. This eliminates metals as a choice for the cylinder. Alternately, the cylinder could be separated into two halves, with a gap between the cylinder halves where the magnets travel, keeping the cylinder material out of the flux path to allow magnetic and conductive materials to be used for the cylinder. In another alternate configuration, the motor can effectively be turned inside out from that shown in FIG. 1 by attaching the coil to the moving piston and mounting the magnets in stationary positions surrounding the outside of the cylinder.

The above mentioned design offers clear efficiency advantages. There are no moving parts in the motor, and only the piston serving as the motor armature is sliding on an air bearing in the pump cylinder. With the axial connection from the piston to a linear motor eliminated, both ends of the piston are used to displace gas in the cylinder for increased displacement potential for a given size pump structure.

A problem with this design meeting the design criteria was discovered. To produce the pressures needed, the piston had to be moved alternately from one end of the cylinder to the other and stopped close to collision with the cylinder heads. To pump a high flow rate of gas with a compact sized pump, these pistons had to oscillate rapidly. In systems with a typical crankshaft, rod, and piston configuration, the pistons are precisely confined to their travel limits by the length of the rigid connecting rod and the stroke length corresponding to 180 degrees of crankshaft rotation. Close clearance between the end of stroke of the piston travel and the cylinder head are easily maintained with those configurations allowing high compression ratios. Eliminating the crank and rod components as in FIG. 1 revealed the problem of accurately controlling the position of the untethered piston, which affects pump performance.

A possible solution was to detect the position of the piston at all times, that a feedback control loop could be devised that moved the piston faithfully through a position sequence sweeping the length of the cylinder, stopping close to the head, reversing direction, sweeping the cylinder in the opposite direction, stopping close to the other head in a continuous cycle. By comparing the actual positions of the piston to a desired pattern of position sequence and generating position correcting forces, position errors could be continuously corrected to maintain a desired pattern of motion. The piston position could be inferred by monitoring the magnetic field of the permanent magnets that moved with the pistons. Hall sensors could produce electrical signals in proportion to the position of the magnet sensed through the cylinder wall. Alternately, the transparent glass cylinder could allow the position to be determined optically. These methods were tried, and a control system was produced that did indeed control the piston movement. Air was pumped with this scheme, but the efficiency was disappointingly low compared to desired design criteria. An analysis of the electrical current input waveform as it changed relative to the piston position revealed critical data. A large amount of current was being used toward the ends of the strokes to decelerate the piston to a stop, and then to accelerate the piston in the opposite direction. The piston with the embedded magnet had significant mass, and was repeatedly and rapidly being accelerated to a maximum velocity then decelerated to a stop just short of collision with the head, and then accelerated in the opposite direction and again decelerated at the other end. These rapid accelerations and decelerations required large amounts of force produced by proportionally large currents in the coil.

Any coil wound with electrical wire above superconducting temperatures has an electrical resistance R. Power P is lost to heat in the coil when a current i is flowing according to $P=i^2R$. The large acceleration and deceleration forces were requiring proportionally large currents that were having a squared effect on the power lost to heat. These currents were contributing nothing to the pumping of the gas, only stopping and reversing the piston direction of travel just short of collision with the heads. Work to reduce R in the coil was not practical to reduce R enough to offset the power loss due to these large currents.

A first improvement was tried that involved the use of mechanical springs. Springs were attached to the piston assembly to produce forces acting to return the piston to the center of its stroke path from any off center position. This formed a classic spring and mass system in which energy was transferred to the spring as it compressed while decelerating the piston as it approached either head. After the piston came to a stop with the spring compressed, the energy was returned to the piston from the spring as it applied force on the piston accelerating it back toward the center of the cylinder.

This created is a simple oscillating mass and spring system with an oscillation frequency given by $f=0.159(k/m)^{0.5}$, where k is the combined spring constant and m is the mass of the piston assembly. The mass will oscillate at a steady frequency from one end of the cylinder to the other without the need for external energy to accelerate and decelerate the piston. Energy applied to this system, synchronized with the natural oscillation frequency, could be entirely directed toward pumping the gas and overcoming remaining friction losses. Testing showed that efficiency was much improved by adding the springs, but the overall efficiency was still short of the design criteria. The springs create noise, and generate heat, thus leading to the conclusion that the springs were consuming energy. Concerns arose that the spring metal could fatigue and break during long run times.

A second improvement was constructed using the repelling forces of like magnetic poles to provide the useful spring effect. This eliminated the energy losses, noise, and possible fatigue related failure modes of mechanical springs. Magnets were mounted on the heads and piston of the pump with their poles aligned with the like poles of the piston magnets. This repelled the pistons toward the center of the cylinder with forces similar to the mechanical springs in the previous attempt.

Figure 2:
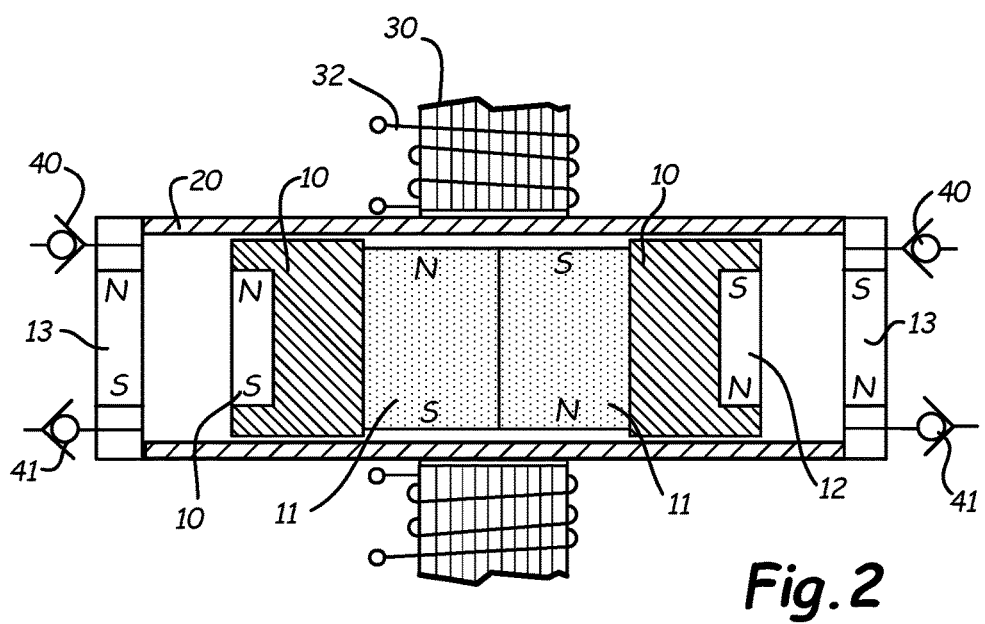
FIG. 2 is a cross sectional view of an alternate embodiment of a pump

FIG. 2 shows the pistons 10 with magnets 12 added, and shows magnets 13 added at the ends of the cylinder. These magnets are polarized across their diameter as are the piston magnets 11. On each end of the piston, magnets 11, 12, and 13 are all positioned rotationally so those like poles align causing them all to repel each other. Magnets 12 could be eliminated in configurations with magnets 13 able to extend into a hallowed center of graphite piece of piston 10 in the area where magnets 12 were removed. Magnets 13 would then repel magnets 11.

In addition to repelling the piston toward the center of the stroke as desired, these magnets, when just slightly misaligned rotationally, such as when the pistons rotated slightly in the cylinder, create an undesirable rotational force on the piston acting to turn the piston so that opposite magnetic poles moved rapidly toward alignment with the head magnets causing them to attract instead of repel. To counter this effect, the attraction forces between the piston magnet poles and the steel core are utilized. By providing gaps between the poles of the iron core where it surrounds the magnets, the magnetic flux paths are focused toward the steel core and away from the gaps. As the poles of the magnet rotate away from the core and toward the gaps, the flux lines are stretched and a strong rotational force is generated to rotate the magnet poles back to being centered under the core poles. By adjusting the size of the gap, this force is made to be much stronger than the opposing force of off center head magnet for small rotational misalignments. The resulting magnet assembly is now rotationally stable.

Figure 3:
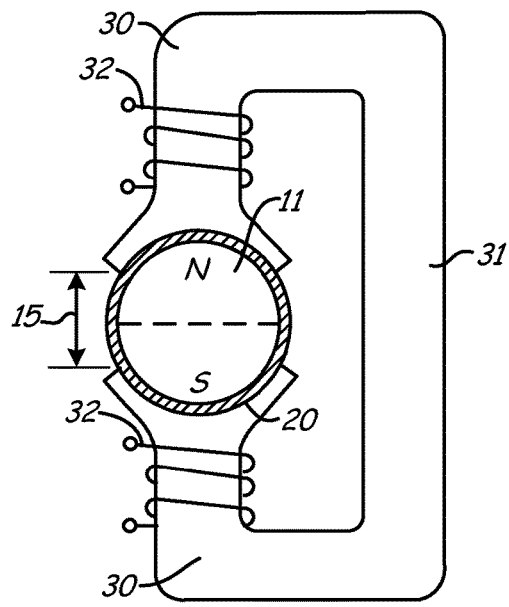
FIG. 3 is an elevation view of the pump in either FIG. 1 or FIG. 2.

FIG. 3 shows the assembly of FIG. 2 from an end view. The north and south poles of magnet 11 are attracted to the flux path 31 made of steel laminations 30. Any rotation away from the poles centered on the flux path as shown generates a rotational force returning the poles of magnet 11 to the centered position on flux path 31.

The size, shape, and positions of the steel core, magnets, and coil wire number of turns were designed and optimized using a magnetic finite element analysis program from Solid Works called Cosmos. Steel core geometry was adjusted to keep magnetic flux densities below the saturation limits of the chosen steel alloy while holding the size of the core to a minimum. The size, shape, and positions of the permanent magnets was adjusted to produce the greatest amount of piston force for a given coil current and number of wire turns in the coil. A large range of pump sizes and capacities using the configurations disclosed here can be designed and optimized using Cosmos or similar magnetic analysis programs. This can save a lot of work compared to searching for optimal magnetic circuit geometries through trial and error steps using real hardware.

Some undesirable behavior was recognized in the updated design. The reciprocating mass of the piston and magnet assembly was large enough to cause undesirable vibration of the pump assembly as it oscillated in the cylinder. The piston magnets had significant mass and presented a lot of vibration force to the system as they were accelerated and decelerated by the magnets 13. If the pump framework was mounted solidly to a mass much greater than that of the piston then the vibration would not have been an issue. According to the design criteria, the pump was part of a light weight portable device having minimal mass so the vibration needed to be greatly reduced by other means. A good solution to this problem was presented in the idea of making two identical but half capacity copies of the pump and rigidly connecting them to each other so that the two pistons were on a common axis of travel. The two pistons were then driven in opposite directions at all times so that the forces causing the vibration should always be exactly opposite each other and be summed to zero at the rigid connection between the two pumps.

The design of counter driven pistons created another issue. The travel of the two pistons needed to be controlled in opposition 180 degrees out of phase for the vibrations to be canceled. The dynamic stability of the system was found to gravitate toward a running mode with the two pistons preferring anything but the 180 degrees out of phase motion when the common attachment point of the two pump halves was allowed any amount of movement. The analysis of this effect involves three moving bodies: the two pistons and the common attached hardware. Three body oscillating systems are known to be very difficult to analyze. The analysis was avoided when it was discovered that the solution was to produce dynamic forces acting on the two pistons that would push them toward the 180 degree phase relationship and be stronger than the forces of the three body problem pulling them out of the 180 degree position. Prior to analyzing, the coils for the two pump halves were wired in series so that they would always be presented with equal current waveforms and therefore equal forces. However, a current that would grow more unequal in magnitude as the pistons slipped away from the 180 phase relation generates the needed force difference to counter this phase slippage problem. This was accomplished by connecting the coils from the two pump halves in parallel instead of in series. In this way, when one piston would slip a little ahead of the other it would draw less current from the power source and the one that was lagging would naturally draw more current. This would generate magnetic forces acting to slow down the one that was getting ahead and speed up the one that was lagging. The resulting dynamic stability with the coils wired in parallel was tested and found to reliably maintain piston motions near the desired 180 degree phase relationship.

Figure 4:
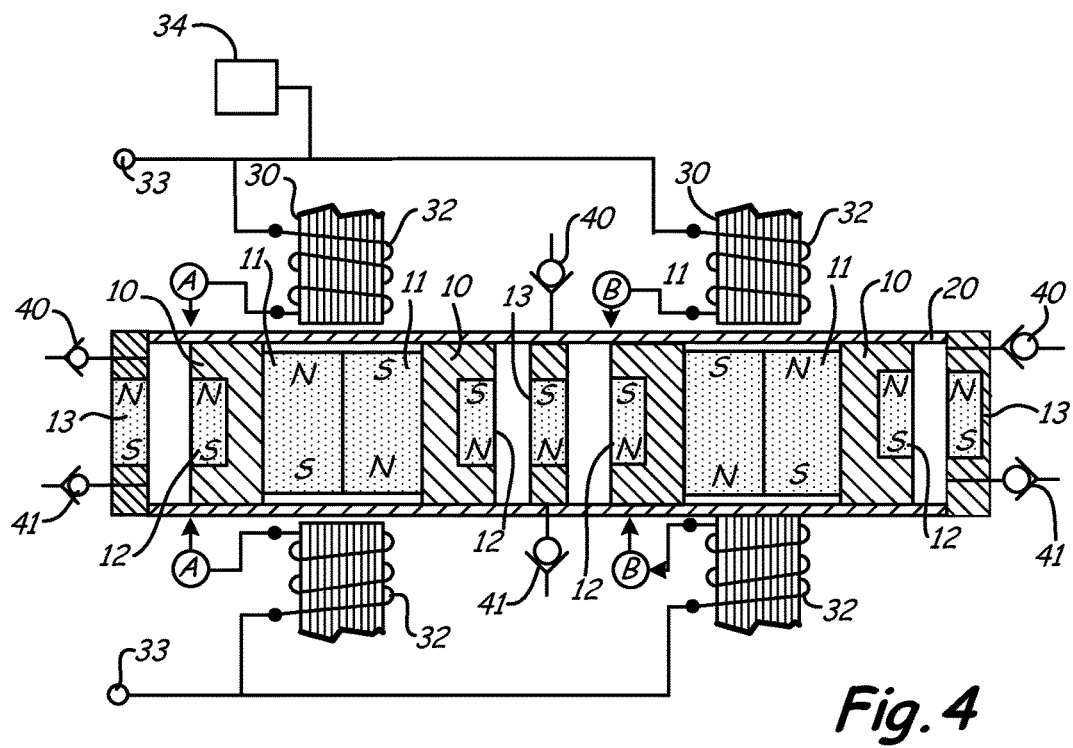
FIG. 4 is a cross sectional view of the pump of FIG. 2 combined with a second identical copy joined at the center of the assembly.

FIG. 4 shows the pump assembly of FIGS. 2 and 3 combined with a second identical copy, and with the two copies joined at the center. Coils 32 and magnets 11 are all polarized as shown in FIG. 4 so that the two piston assemblies will always travel in opposing directions. Coils are connected in series at points A for the left coil pair and B for the right pair. These connected pairs are then connected between right and left pump sections in parallel as discussed. Where the two magnets 13 would have come together at the center of this assembly one of them is eliminated. In some embodiments, the components may be sized so that no magnets 13 are needed in the center. Magnets 11 may produce enough repelling force between each other to push the pistons toward their centers of stroke travel.

The next addition to the pump involved the control scheme that produced the coil driving current waveform. This waveform would be presented to electrical connections 33 in FIG. 4. The most efficient current waveform to drive the coils with the least electrical loss for a given pneumatic power output was researched. The available position sensors that were being used to send piston position to the control scheme were not accurate enough to control the piston stroke to stop close enough to the heads of the cylinder as needed to produce a high pressure ratio between the input and output of the pump. A good sensor scheme could probably have been developed using available methods and hardware, but the new pump design was being distorted by magnetic and electrical interference radiating from the magnetic coils of the pump. A better scheme to accurately control piston travel was researched.

Research revealed that the most efficient coil current waveform that could be provided to the pump coils was one in which the coil current was always in proportion to the instantaneous piston speed at each position within a piston stroke. The simple, though less than rigorous explanation for this, is that mechanical power has units of (force×distance)/time. This is also commonly designated as (force×speed). Electrical power is (volts×amps). Amps produce a proportionate force on the pistons, but higher amps causes more power loss from heat in the coil in proportion to $i^2(R)$— where i is the coil current and R is the coil resistance. Design criteria suggested that the pump apply higher current to produce higher force when the piston is moving the fastest so that the resulting mechanical power (force×speed) is maximized. When the piston is moving slowly, high currents are wasteful because electrical losses are high while the mechanical energy produced is small due to the small speed multiplier. However, if all the current were concentrated at this highest speed point of the piston it would need to be a very strong current pulse to provide enough energy to launch the piston through the entire stroke. This current pulse when squared would produce a large loss when multiplied by the coil resistance. As a result, the current was spread over the entire stroke in proportion to the speed of the piston in the pump apparatus.

The control scheme was developed to keep the current waveform in proportion to the piston speed, and required no piston position sensor. The control scheme only needed to detect the moment in time when the piston paused at the end of its stroke and began to travel in the opposite direction due to the repelling forces of the magnets. The current was matched to the piston speed at all times during the stroke. The piston speed throughout the stroke path can be somewhat complex, as the piston is accelerated and decelerated by the interaction of the magnets with a nonlinear force verses distance relationship. Also, the cylinder pressures and the magnetic core impart forces that affect the piston speed.

A digital control algorithm executed by a microcontroller was developed. The trip of the pistons from one end of the cylinder to the opposite end was defined as a stroke. Each stroke was divided into 128 time steps so that at each step a unique coil current could be selected and presented to the coils. Before the last few steps of each stroke, the current was turned off, and the piston was allowed to coast to a stop and reverse its travel due to the effect of the repelling magnets. With the piston coasting and not being driven by current, the piston magnets are causing flux change in the core that induces a voltage in the coil. When the piston stops and changes direction, the induced coil voltage goes to zero and then changes polarity as the direction changes. This is sensed by electronic comparator 34 connected to monitor the polarity of the coil voltage and converted to a digital zero value for one direction of piston travel and a digital one for the opposite direction. The time duration of the stroke that just ended is measured as the time between this piston direction reversal and the previous reversal at the end of the previous stroke. It is a good prediction that the stroke just ended will be close in duration to the one ready to begin because piston oscillations are rapid and several occur before pump pressure conditions can change significantly for most applications. This gives the starting time and the duration of the next stroke. The coil current waveform will be applied in small steps spanning this time interval.

The measured duration of the stroke just ended was divided by 128 and that result was used for the step time interval to sequence through each element of a list of 128 digitized electrical current values stored in a memory table. The stored current value at each time step was read, and was applied to the pump coils at that time. However, the correct current for each step was unknown because the actual piston speed to be matched at each step was unknown. Only the total stroke time was known. The desired values of each of the 128 current steps was found experimentally by increasing or decreasing a few points at a time while running the pump and monitoring efficiency. This was a trial and error search for the optimal pattern. An acceptable starting pattern approximated a half sine wave with the zero current points aligned with the start and end of each stroke. This pattern was shifted a bit early to compensate for the delay effect of coil inductance acting to slow current change in the coil. The optimal waveform was found experimentally by trial and error to be close to this starting point. The piston speed was originally believed to approximately follow a sinusoidal pattern in time so finding that the optimal current waveform was also sinusoidal provided some proof to the earlier statement that the current should be in proportion to the piston speed for best efficiency. The optimal current values that were found for each of the steps were stored in the memory table and read out one by one as a piston stroke progressed. These defined the duty cycle of a pulse width modulator producing the current levels in the coil. Alternately, an automatic system could have been implemented to find the most efficient current wave form. It could incrementally search by changing each point on the current waveform one at a time in small increments, running the pump a few strokes and comparing the efficiency before and after the change until no further improvements occurred. The manual trial and error steps followed essentially the same process.

Having arrived at the best shape for the current waveform, accurately controlling the stroke length of the pistons and the power output of the pump was possible by multiplying each point in the current waveform table by a scaling factor that corresponds to the pneumatic work load of the pump and the desired stroke length. In application for the design criteria, the power output of the pump had to vary as the pneumatic process steps it was involved in cycled through a repeating sequence. Electronically monitoring the changing pressure differences between the pump input and output ports and using the data as a scaling factor for the current waveform table entries could maintain a desired stroke length as the work load of the pump changed.

Minimizing the current required to operate the pump as disclosed is important for efficiency with current squared in the power loss equation $P=i^2(R)$. Reducing the coil resistance R is less important since it contributes only linearly to the losses but is still significant and worth reducing. The resistance of the coil is inversely proportionate to the cross sectional area of its wire. Larger wire diameters have larger sectional areas and less resistance for a given length so they result in a coil with less resistance for a given length of wire. As the wire size is increased to reduce resistance, its area and the total volume occupied by the wire increases. This increased volume can be more easily accommodated with the rather open structure of the flux path in FIG. 3 than it can in other typical motors. In other motors the coils are more confined to narrow slots in their armature or stator components.

Hysteresis and eddy current losses in the steel flux paths were kept to low levels by using a laminated silicon steel core structure as is commonly found in electrical transformers and motors in the prior art. A sintered metal core may also be a good core choice for some applications.

The pump structure disclosed herein merged pump components with motor components. The pump piston is the moving armature of the motor. The motor therefore needs no armature, bearing structure, or mechanical linkage connecting it to the pump piston. The design was developed toward the goals of energy efficiency, but the elimination of these typical components found in other motor driven pumps also reduced overall pump weight and size. The overall number of moving parts was reduced to one or two low friction piston components providing improved reliability and durability relative to pumps with more moving parts and higher friction.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of controlling a fluid pump, the pump comprising a plurality of oscillating pistons that travel along a central axis of a piston sleeve, the method comprising:
   providing the plurality of oscillating pistons of similar mass within the piston sleeve wherein each piston of the plurality of oscillating pistons has a first end and a second end and at least one magnet, and wherein the piston sleeve has a first end with a first permanent magnet and a second end with a second permanent magnet along the central axis of the piston sleeve;
   repelling one of the plurality of oscillating pistons from the first end of the piston sleeve by facing like poles of the one of the plurality of oscillating pistons and the first permanent magnet;
   repelling another of the plurality of oscillating pistons from the second end of the piston sleeve by facing like poles of the other of the plurality of oscillating pistons and the second permanent magnet;
   positioning adjacent pistons to be 180 degrees apart in phase oscillations;
   providing an electric coil for each piston;
   determining the position of adjacent pistons; and
   adjusting the current of the electric coils for the pistons to maintain the 180 degree difference in phase between oscillations of adjacent pistons.

2. The method of claim 1 wherein each of the plurality of oscillating pistons comprises:

a graphite body; and at least one permanent magnet.

3. The method of claim 1 wherein the piston sleeve is constructed from a low electrical conductivity material.

4. The method of claim 1 wherein determining the position of each of the plurality of oscillating pistons is done with an electronic comparator sensor.

5. The method of claim 1 wherein determining the position of each of the plurality of oscillating pistons is done by monitoring pressure differences between a pump input and output ports.

6. An apparatus for pumping and compressing fluids, comprising:

a cylinder body comprising a central axis and an inner surface that creates an inner volume with the cylinder body having a first magnet at a first end and a second magnet at a second end;

a first piston and a second piston of similar mass within the cylinder body with the first and second pistons being able to oscillate along the central axis, the first piston having a third magnet that repels the first magnet at a first end of the cylinder body and the second piston having a fourth magnet that repels the second magnet at a second end of the cylinder body; and wherein the first and second pistons are driven by magnetic forces generated by electrical currents to oscillate the first and second pistons with a similar stroke length while maintaining a 180 degree difference between the oscillations of the first and second pistons.

7. The apparatus of claim 6 wherein the electrical currents are carried by two electrical coils, each coil corresponding to one of the two pistons.

8. The apparatus of claim 6 wherein the two electrical coils are connected in parallel to each other such that if the first piston becomes more than 180 degrees ahead of the second piston, the second piston will receive more current to increase the speed of the second piston to maintain the 180 degree difference between the oscillations of the first and second pistons.

9. A method of pumping and compressing a fluid comprising: oscillating a piston between a first end of a cylinder and a second end of the cylinder using oscillating magnetic forces, the piston having a first set of magnets at a center to interact with an electric coil creating the oscillating magnetic forces wherein the oscillating of the piston between the first end of the cylinder and the second end of the cylinder is configured to pump and compress the fluid, the piston having a second magnet at a first end of the piston and a third magnet at a second end of the piston; repelling the first end of the piston from the first end of the cylinder by facing like poles of the second magnet with like poles of a fourth magnet at the first end of the cylinder; repelling the second end of the piston from the second end of the cylinder by facing like poles of the second magnet with like poles of a fifth magnet at the second end of the cylinder; determining the position of the piston; and adjusting the speed at which the piston oscillates by adjusting the oscillating magnetic forces.

10. The method of claim 9, wherein the cylinder is separated into two equal-length halves with a gap therebetween, the first set of magnets oscillating within the gap.

11. The method of claim 10, wherein the two equal-length halves are not within a flux path formed by the electric coil to allow the cylinder to be constructed from a material that does not have low electrical conductivity.

12. The method of claim 9, wherein determining the position of the piston is done by an electronic comparator sensor.

13. The method of claim 9, wherein determining the position of the piston is done by monitoring pressure differences between a pump input and a pump output in the cylinder.

14. The method of claim 9, further comprising:

adjusting the speed of the piston depending on the position of the piston within the cylinder by adjusting the current within the electric coil with the current being proportional to the speed of the piston.

\* \* \* \* \*